(12) United States Patent  
Morgan et al.

(10) Patent No.: US 7,397,166 B1  
(45) Date of Patent: Jul. 8, 2008

(54) ELECTROACTIVE POLYMER-ACTUATED PERISTALTIC PUMP AND MEDICAL LEAD INCORPORATING SUCH A PUMP

(75) Inventors: Kevin L. Morgan, Simi Valley, CA (US); Anne M. Shelchuk, Cupertino, CA (US); Jeffery D. Snell, Chatsworth, CA (US); Nils Holmström, Järfälla (SE); John R. Helland, Saugus, CA (US)

(73) Assignee: Pacesetter, Inc., Sylmar, CA (US)

( * ) Notice: Subject to any disclaimer, the term of this patent is extended or adjusted under 35 U.S.C. 154(b) by 179 days.

(21) Appl. No.: 11/404,268

(22) Filed: Apr. 12, 2006

(51) Int. Cl.
*H01L 41/08* (2006.01)

(52) U.S. Cl. .................. 310/328; 310/331; 310/800; 417/322

(58) Field of Classification Search ................ 310/328, 310/330–332, 800; 417/322  
See application file for complete search history.

(56) References Cited

U.S. PATENT DOCUMENTS

| | | | | |
|---|---|---|---|---|
| 4,115,036 A | * | 9/1978 | Paterson | 417/322 |
| 4,432,699 A | * | 2/1984 | Beckman et al. | 417/63 |
| 4,449,893 A | * | 5/1984 | Beckman et al. | 417/322 |
| 4,519,751 A | * | 5/1985 | Beckman et al. | 417/322 |
| 5,192,197 A | * | 3/1993 | Culp | 417/322 |
| 5,312,762 A | | 5/1994 | Guiseppi-Elie | 436/149 |
| 6,074,178 A | * | 6/2000 | Bishop et al. | 417/322 |
| 6,314,317 B1 | | 11/2001 | Willis | 604/20 |
| 6,490,483 B2 | | 12/2002 | Willis | 604/20 |
| 6,514,237 B1 | | 2/2003 | Maseda | 604/533 |
| 6,679,836 B2 | | 1/2004 | Couvillon, Jr. | 600/146 |
| 6,696,575 B2 | | 2/2004 | Schmidt et al. | 548/524 |
| 6,712,772 B2 | | 3/2004 | Cohen et al. | 600/561 |
| 6,749,556 B2 | * | 6/2004 | Banik | 600/30 |
| 6,768,246 B2 | | 7/2004 | Pelrine et al. | 310/339 |
| 2001/0029348 A1 | | 10/2001 | Willis | 604/20 |
| 2001/0035723 A1 | | 11/2001 | Pelrine et al. | 318/116 |
| 2002/0022795 A1 | | 2/2002 | Reynolds et al. | 604/20 |
| 2002/0035346 A1 | | 3/2002 | Reynolds et al. | 604/20 |
| 2003/0100839 A1 | | 5/2003 | Cohen et al. | 600/486 |
| 2003/0212306 A1 | | 11/2003 | Banik | 600/30 |
| 2003/0236445 A1 | | 12/2003 | Couvillon, Jr. | 600/114 |
| 2003/0236531 A1 | | 12/2003 | Couvillon, Jr. | 606/113 |
| 2004/0068161 A1 | | 4/2004 | Couvillon, Jr. | 600/143 |
| 2004/0087982 A1 | | 5/2004 | Eskuri | 606/153 |
| 2004/0143160 A1 | | 7/2004 | Couvillon, Jr. | 600/114 |
| 2004/0167375 A1 | | 8/2004 | Couvillon, Jr. | 600/17 |

(Continued)

FOREIGN PATENT DOCUMENTS

WO     WO 00/48669 A1     8/2000

(Continued)

*Primary Examiner*—Mark Budd

(57) ABSTRACT

A peristaltic pump for conveying a fluid comprises a flexible tube having an outer surface and a lumen for carrying the fluid such as a therapeutic agent. The tube has a length defined by opposed ends of the tube, the outer surface of the body carrying a plurality of longitudinally spaced-apart electroactive polymer actuators. The plurality of actuators are adapted to be responsive to electrical signals for energizing the actuators sequentially along the length of the tube to move a lumen pinch-off along the length of the tube to thereby convey the fluid from one end of the tube to the other end by means of a peristaltic pumping action. The peristaltic pump may be incorporated into a medical lead, such as an endocardial pacing lead, carrying at least one electrode.

6 Claims, 4 Drawing Sheets

U.S. PATENT DOCUMENTS

2006/0047318 A1 3/2006 Pastore et al.

FOREIGN PATENT DOCUMENTS

| WO | WO 01/065615 A3 | 9/2001 |
| WO | WO 02/13784 A2 | 2/2002 |
| WO | WO 02/013784 A3 | 2/2002 |
| WO | WO 2004/000403 A1 | 12/2003 |
| WO | WO 2004/014238 A2 | 2/2004 |
| WO | WO 2004/014238 A3 | 2/2004 |
| WO | WO 2004/030554 A1 | 4/2004 |
| WO | WO 2004/075953 A1 | 9/2004 |

* cited by examiner

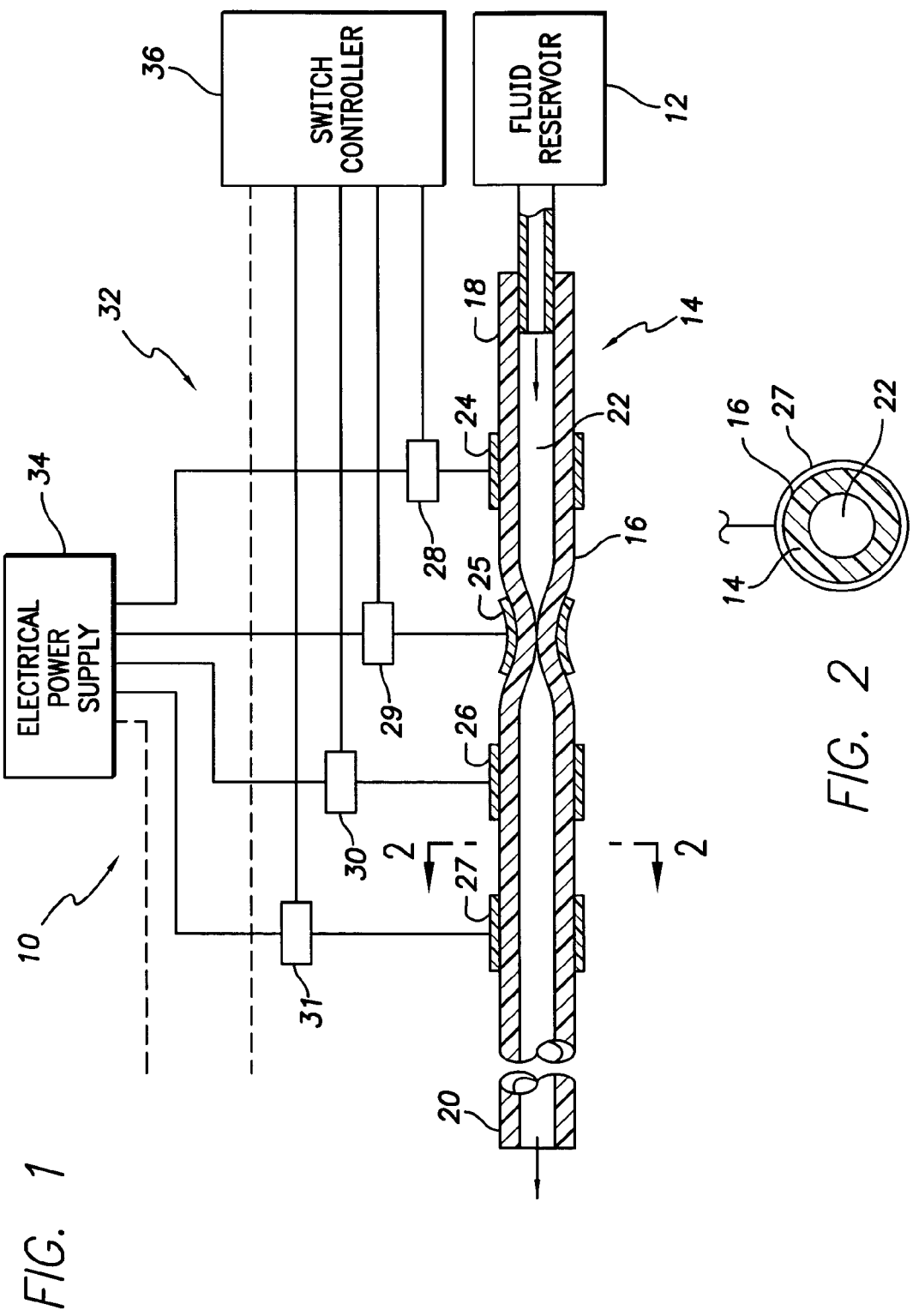

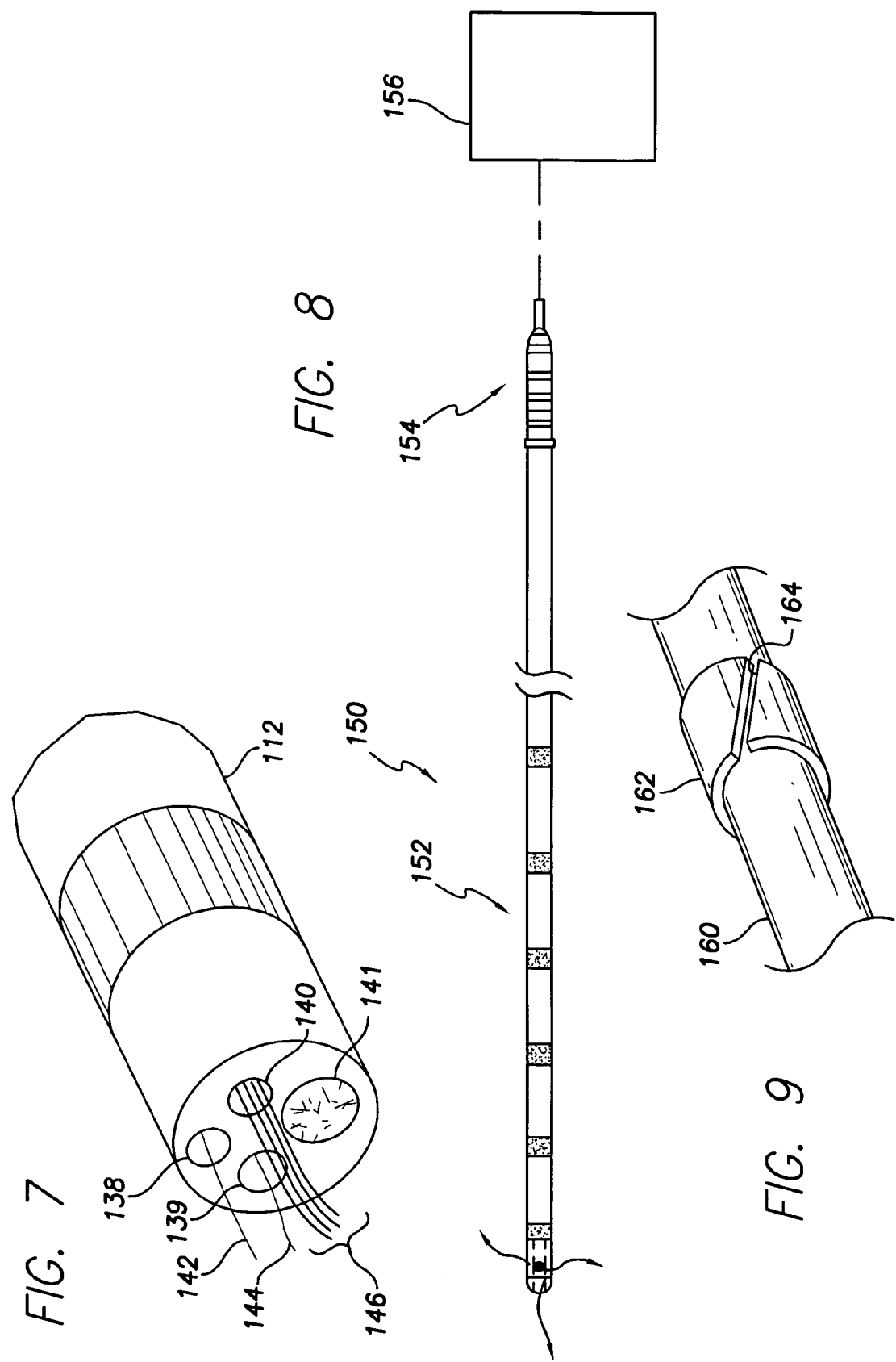

ELECTROACTIVE POLYMER-ACTUATED PERISTALTIC PUMP AND MEDICAL LEAD INCORPORATING SUCH A PUMP

FIELD OF THE INVENTION

The present invention relates generally to peristaltic pumps and particularly to an electroactive polymer-actuated peristaltic pump. The invention also relates to such a pump for delivering a therapeutic agent from a reservoir to a selected body site.

BACKGROUND OF THE INVENTION

Mechanical peristaltic pumps are well known. By way of example, such pumps may be used for the infusion of medical fluids into, or for the removal of body fluids from, a patient. These systems typically comprise a length of flexible tubing within a compression chamber defined by a compression surface and a rotor assembly. The rotor assembly includes a plurality of parallel rollers disposed about the periphery of a rotor. With the rotor assembly rotating, the rollers are biased against the flexible tubing that is backed up by the compression surface. The rollers successively pinch off the tubing, advancing the pinch-off position so as to progressively move the fluid within the tube and into or from the patient's body at a controlled rate that is determined by various design and operational parameters such as the angular velocity of the rotor assembly.

Electroactive polymer (EAPs), also referred to as electrically conductive or conducting polymers, are flexible materials capable of converting energy in the form of electric charge and voltage to mechanical force and movement. Thus, these materials are able to change shape in response to electrical stimulation. Common electroactive polymers include polyaniline, polypyrrole and polyacetylene. It is well known that dimensional changes may be effected in these polymers by the mass transfer of ions into or out of the polymer that causes expansion or contraction of the polymer.

Ionomeric polymer-metal composites (IPMC) comprise a subcategory of ionic EAPs. The detailed description, below, will be directed toward these but the invention is not limited to them.

A typical IPMC consists of a thin (200 micrometers) polymer membrane with a metal electrode (5-10 micrometers thick) plated on each face. The polyelectrolyte is neutralized with counter-ions, balancing the charge of the anions covalently fixed to the membrane. When an IPMC is hydrated and stimulated by a small voltage (1-5 V), both the fixed anions and the mobile counter-ions are subjected to the electric field. The counter-ions diffuse toward one of the electrodes and, as a result, the composite undergoes a fast bending deformation toward the anode. The bending is the result of increased stiffness along the cathode and decreased stiffness along the anode. Examples of IPMCs include perfluorosulfonate (Nafion) and perfluorocarboxylate (Flemion) coated with metal ions such as platinum or gold. Another subcategory of ionic EAPs comprises ionic polymer gels (IPG) such as polyacrylonitrile (PAN).

Electrical stimulation of the tissue of a patient's body for medical purposes is well known. An example of a device for this purpose is the cardiac pacemaker. In the pacemaker context, as well as other body stimulation contexts, the stimulation is delivered to a desired body site by an electrode-carrying lead.

Interactions between the lead and the patient's body can vitiate the desired effects of the stimulation. For example, material reactions and healing may encourage fibrosis. In the pace making context, fibrosis is believed to be a major factor in the increase in chronic stimulation threshold that is usually experienced. Also, mechanical trauma may result in inflammation of the tissue to be stimulated. Such inflammation may alter the response of the tissue to the stimulation energy, both acutely and chronically.

Other interactions between the lead and the body, while not directly affecting the response of the tissue to the stimulation energy, can result in the occurrence of undesirable events. For example, the placement of a pacing lead may induce a cardiac arrhythmia. Furthermore, the presence of the lead may also promote thrombus formation. These interactions have been long recognized and efforts have been made to ameliorate their consequences. For example, therapeutic agents in the form of drugs may be released in vivo to counter trauma caused by an implanted device such as a cardiac pacemaker lead. Because such trauma typically occurs in the region in which the distal end of the pacing lead contacts the cardiac tissue, a pacing lead may have a cavity or collar at the distal end of the lead containing a drug to counter undesirable interactions between the lead and the tissue. Steroid-eluding leads having a tip electrode housing a variety of matrix materials with a drug being stored in, and dispensed from, the tip electrode, are also well known. Anti-inflammatory steroids may also be embedded within a thin coating of a hydrophilic polymer overlying an implantable porous stimulating electrode. The steroid simply diffuses from the polymeric layer into the adjoining tissue to reduce growth of connective tissue. Body implantable pacemaker leads utilizing an osmotic pump to control dispensing of a therapeutic agent or drug are also known.

SUMMARY

In accordance with one specific, exemplary embodiment of the invention, there is provided a peristaltic pump for conveying a fluid, the pump comprising a flexible tube having an outer surface and a lumen for carrying the fluid. The tube has a length and opposed ends, the outer surface of the body carrying a plurality of longitudinally spaced-apart electroactive polymer actuators. The actuators are adapted to be responsive to electrical signals for energizing the actuators sequentially to move a lumen pinch-off along the length of the tube to thereby convey the fluid from one end of the tube to the other end by means of a peristaltic pumping action.

In accordance with another specific, exemplary embodiment, there is provided a device for delivering a therapeutic agent, the device comprising an elongated flexible tubular body having an outer surface, a distal end and a proximal end. The tubular body further defines a lumen extending between the distal and proximal ends, and the outer surface of the body carries a plurality of longitudinally spaced-apart electroactive polymer actuators. The actuators are adapted to be responsive to electrical signals for successively energizing the actuators to sequentially pinch the tubular body and to thereby convey a therapeutic agent by a peristaltic pumping action via the lumen from the proximal end to the distal end of the body, the therapeutic agent being thereby ejected from the distal end.

Pursuant to yet another specific, exemplary embodiment of the invention, there is provided an endocardial medical lead comprising a flexible, tubular, electrically insulating, biocompatible, biostable lead body, the lead body including a distal end carrying at least one electrode, a proximal end carrying an electrical connector assembly, and an intermediate portion coupling the distal and proximal ends. The intermediate portion carries a plurality of longitudinally spaced-apart electroactive polymer actuators, the lead body containing electrical conductors connecting electrical contact means on the electrical connector assembly with the at least one electrode and the plurality of electroactive polymer actuators. The electroactive polymer actuators are adapted to be responsive to electrical signals transmitted from the electrical connector assembly for energizing the plurality of electroactive polymer actuators sequentially along the intermediate portion of the tubular lead body. A lead body pinch-off is thereby moved along the intermediate portion to convey a therapeutic agent from the proximal end of the lead body to the distal end of the lead body by means of a peristaltic pumping action, the agent being discharged from the distal end of the lead body.

An advantage of the invention is that it provides a peristaltic pumping action without the use of mechanical elements.

BRIEF DESCRIPTION OF THE DRAWINGS

The foregoing and other objects, features and advantages of the invention will be evident to those skilled in the art from the detailed description below, taken together with the accompanying drawings, in which:

FIG. 1 is a schematic representation, partly in cross section, of a peristaltic pump system in accordance with one aspect of the present invention;

FIG. 2 is a transverse cross section of a portion of the system of FIG. 1 as seen along the line 2-2 in FIG. 1;

FIG. 7 is a perspective view of a portion of the lead system shown in FIG. 6;

FIG. 8 is a schematic representation of an endocardial, bipolar pacing and therapeutic agent-dispensing lead system in accordance with yet another, specific, exemplary embodiment of the invention; and FIG. 9 is a schematic representation of a portion of a peristaltic pump in accordance with still another embodiment of the invention.

DETAILED DESCRIPTION OF THE INVENTION

Figure 3:
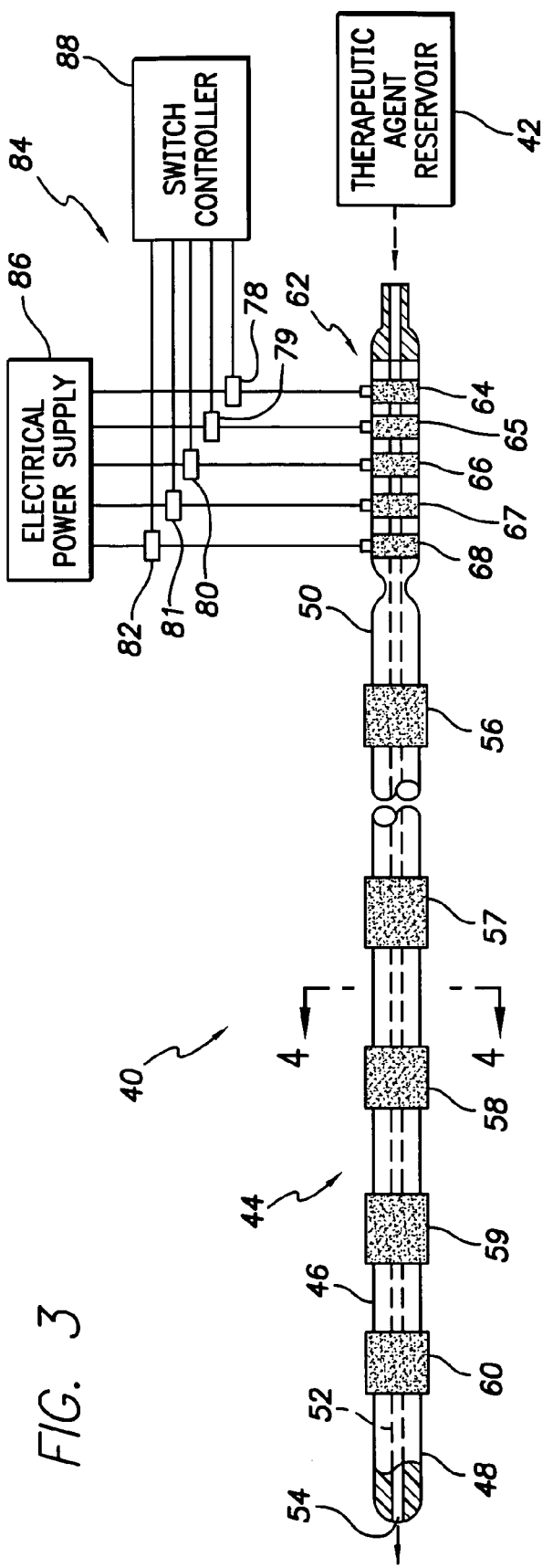
FIG. 3 is a schematic representation, partly in cross section, of a peristaltic pump system in accordance with one specific, exemplary embodiment of the present invention, the system including a medical device in the form of a catheter for delivering a therapeutic agent to a selected body site.

The following description is of a best mode presently contemplated for practicing the invention. This description is not to be taken in a limiting sense but is made merely for the purpose of describing the general principles of the invention whose scope may be ascertained with reference to the appended claims.

FIGS. 1 and 2 show a system 10 in accordance with one specific, exemplary embodiment of the invention for peristaltically conveying a fluid from a fluid reservoir 12. The system 10 comprises an elongated, flexible tube 14 having an outer surface 16 and opposed ends 18 and 20. The tube 14 is preferably fabricated of a soft, flexible material such as silicone rubber, polyurethane, or the like. The tube defines a lumen 22 extending between the opposed ends 18 and 20. The lumen 22 at end 18 of the tube 14 communicates with the fluid reservoir 12.

The outer surface 16 of the tube 14 carries a plurality of longitudinally spaced-apart electroactive polymer actuators 24-27 each of which, in accordance with the specific embodiment shown in FIGS. 1 and 2, comprises an annular cuff or band encircling the outer surface 16 of the tube. The number of cuffs may vary. Although it will be evident that a series of cuffs is preferred, a single cuff may be sufficient. Each of the cuffs 24-27 may be constructed as a separate element that is slid into place along the length of the outer surface of the tube 14. Preferably, however, each cuff is formed by coating it on the outer surface 16 of the tube 14. It will be evident as the description proceeds that the flexible tube 14 itself may be constructed entirely of an electroactive polymer material although in the preferred construction of the invention multiple electroactive polymer actuators are spaced-apart along the length of the tube, as shown in FIGS. 1 and 2.

Each EAP actuator cuff is electrically energized to locally constrict or pinch off the flexible tube. In operation, the longitudinally spaced-apart electroactive polymer actuator cuffs 24-27 are responsive to electrical control signals phased so as to sequentially energize the plurality of actuators along the length of the tube to advance the pinch-off position so as to progressively convey the fluid along the length of the tube by means of a peristaltic pumping action from the reservoir 12 at the end 18 via the lumen 22 to the tube's other end 20 from which the fluid is discharged. By way of illustration, the electroactive polymer actuator cuff 25 is shown in its energized, pinch-off state.

More specifically, the cuffs 24-27 are electrically connected via switches 28-31, respectively, to an EAP actuator drive 32 comprising an electrical power supply 34 and a programmable switch controller 36 coupled to close the switches 28-31 in succession to sequentially energize the electroactive polymer actuator cuffs 24-27 to achieve the desired peristaltic pumping action. The frequency, phasing, duration and other parameters of the energization of the actuator cuffs may be programmed; such energization parameters will depend upon the number of actuators, the desired flow rate, and so forth. Programmable controllers for performing these functions are well-known in the art.

Figure 4:
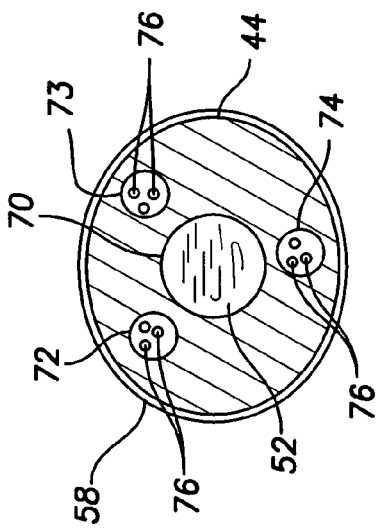
FIG. 4 is a cross section of the system shown in FIG. 3 as seen along the line 4-4 in FIG. 3.

FIGS. 3 and 4 show a system 40 in accordance with a specific, exemplary embodiment of the invention for conveying a therapeutic agent from a reservoir 42 to a selected anatomical body site. The system 40 comprises an elongated, flexible tubular body or catheter 44 having an outer surface 46, a distal end 48 and a proximal end 50. The catheter 44 is preferably fabricated of a flexible, biocompatible, biostable material such as silicone rubber, polyurethane, or the like. The catheter 44 defines a lumen 52 extending between the proximal and distal ends of the catheter. The lumen 52 at the proximal end of the catheter communicates with the reservoir 42 containing a supply of the therapeutic agent that is to be delivered via the lumen to at least one discharge port 54 in the distal end of the catheter.

The outer surface of the catheter carries a plurality of longitudinally spaced-apart electroactive polymer actuators 56-60 each of which comprises an annular cuff or band encircling the outer surface 46 of the catheter. Each of the cuffs 56-60 may be constructed as a separate element that is slid into place along the length of the catheter. Preferably however, each cuff is formed by coating an electroactive polymer on the outer surface 46 of the catheter. It will be evident as the description proceeds that the flexible catheter itself may be constructed entirely of an electroactive polymer material although in the preferred construction of the invention multiple electroactive polymer actuators are spaced-apart along the length of the catheter body, as shown in FIGS. 3 and 4.

As seen in the embodiment of FIGS. 1 and 2, the longitudinally spaced-apart electroactive polymer actuator cuffs 56-60 are responsive to electrical control signals phased so as to sequentially energize the plurality of actuators along the length of the catheter to locally constrict or pinch off the catheter body; advancement of the pinch-off position along the length of the catheter conveys the therapeutic agent by means of a peristaltic pumping action from the reservoir 42 at the proximal end 50 via the lumen 52 to the catheter's distal end 48 from which the agent is dispensed through the port 54. In this connection, in accordance with the preferred embodiment shown in FIGS. 3 and 4, the proximal end of the catheter carries a connector assembly 62 comprising a plurality of longitudinally spaced-apart contacts 64-68 electrically connected to the electroactive polymer actuator cuffs 56-60, respectively. As best seen in FIG. 4, the catheter 44 may comprise a multi-lumen 70 structure that includes a therapeutic agent-conveying lumen along with one or more lumens such as the three lumens 72-74 carrying electrical conductors 76 coupling the connector assembly 62 contacts 64-68 with corresponding electroactive polymer actuator cuffs.

The electrical connector assembly 62 may be received within a receptacle (not shown) carrying a plurality of terminals engaging associated ones of the contacts 64-68 on the connector assembly. The terminals are electrically connected via switches 78-82 to an EAP actuator drive 84 comprising an electrical power supply 86 and a programmable switch controller 88 for closing the switches 78-82 in succession to sequentially energize the electroactive polymer actuator cuffs 56-60 to achieve the desired peristaltic pumping action. The frequency, phasing, duration and other parameters of the energization of the actuators may be varied; such energization parameters will depend upon the number of actuators, the desired flow rate, and so forth, and will be apparent to those skilled in the art.

Figure 5:
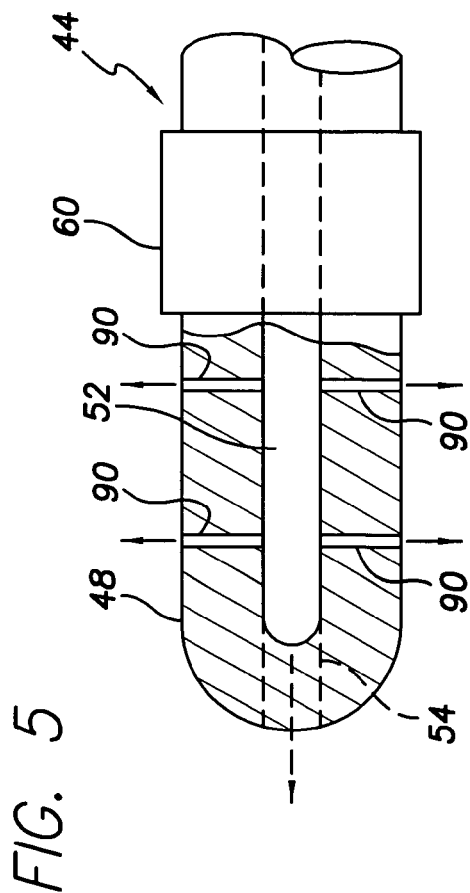
FIG. 5 is a side view, partly in cross section, of the distal end of a medical device in the form of a catheter forming part of another specific, exemplary embodiment of the invention.

With reference to FIG. 5, instead of the therapeutic agent exiting the catheter 44 in a longitudinal direction via a discharge port 54 in the distal end 48 thereof, it will be evident that in addition to or as an alternative to such a discharge scheme, one or more passages 90 may be formed in the distal end of the catheter body in communication with the lumen 52 to discharge the therapeutic agent outwardly from the side of the distal end 48.

A system according to the invention may simply comprise a catheter along the lines shown in FIGS. 3 and 4. Alternatively, a system pursuant to the invention may incorporate a body tissue stimulating lead such as an intravenous pacing lead for electrically stimulating selected body tissue and/or sensing the electrical activity thereof.

Figure 6:
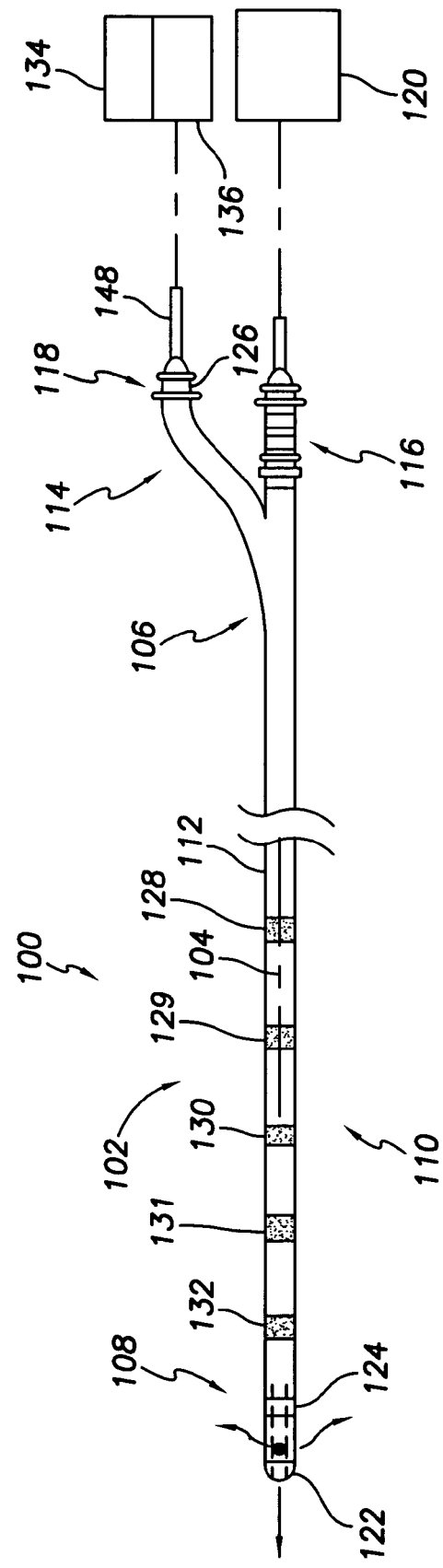
FIG. 6 is a schematic representation of an endocardial, bipolar pacing and therapeutic agent-dispensing lead system in accordance with another, specific, exemplary embodiment of the invention.

For example, referring to FIGS. 6 and 7, there is shown a bipolar, endocardial pacing and therapeutic agent delivery system 100. The system 100 comprises a lead 102 having a longitudinal axis 104, a proximal end portion 106, a distal end portion 108 and an intermediate portion 110 connecting the end portions. The lead 102 comprises a multi-lumen, tubular, insulating housing or sheath 112 made of an insulating, biocompatible, biostable flexible elastomeric material such as silicone rubber or polyurethane. The proximal end portion 106 of the lead comprises a bifurcated electrical connector assembly 114 comprising a first connector portion 116 and a second connector portion 118. The first connector portion 116, which may conform to the IS-1 connector standard, is adapted to transmit electrical signals between a pulse generator or pacemaker 120 and a bipolar electrode pair carried by the distal end portion 108 of the lead. In well-known fashion, the electrode pair may comprise a tip electrode 122 and a ring electrode 124 positioned proximally of the tip electrode. The second connector portion 118 of the connector assembly 114 comprises a multi-contact connector 126 whose contacts are electrically connected with corresponding or associated electroactive polymer actuator cuffs 128-132 disposed in longitudinally spaced-apart relationship along the intermediate portion 110 of the lead along the lines described in connection with FIGS. 3 and 4. Electrical signals generated by an EAP actuator drive 134 and applied sequentially to the electroactive polymer actuator cuffs 128-132 cause the cuffs to contract and to pinch off the flexible housing 112 in succession to transport a therapeutic agent from a reservoir 136 to the lead's distal end portion 108 from which the agent is dispensed axially and/or laterally as previously explained.

The multi-lumen housing 112, as best seen in FIG. 7, comprises, in accordance with an exemplary embodiment, four parallel lumens 138-141 extending the length of the lead. By way of example only, the lumens 138 and 139 may be used to house electrical conductors 142 and 144 connecting contacts on the first connector portion 116 with the tip and ring electrodes 122 and 124. The lumen 140 may contain electrical conductors 146 connecting contacts on the second connector portion 118 with various ones of the electroactive polymer actuator cuffs 128-132. The lumen 141 may function as a conduit for conveying the therapeutic agent from the second connector portion 118 to the distal end of the lead. Along the lines previously described, the therapeutic agent may be discharged axially through one or more ports formed in the tip electrode or, alternatively, the agent may be dispensed from one or more passages formed in the side of the lead along the distal end portion thereof.

The second connector portion 118 may include a tubular pin 148 whose lumen communicates with the drug delivery lumen 141 in the lead housing. The therapeutic agent may thus be delivered from the reservoir 136 to which the connector portion 118 is attached. The pacemaker, EAP actuator drive and reservoir may be separate units or they may be integrated into a single assembly.

In one form of the invention, the pin 148 forming part of the second connector portion 118 may be solid with the therapeutic agent being stored in the lumen 141 of the lead. The reservoir 136 would accordingly not be used in this form of the invention and the volume of therapeutic agent available to medicate the target body site would be limited to that contained within the lumen 141 of the housing.

FIG. 8 shows in schematic form a bipolar, endocardial pacing and therapeutic agent delivery system 150 in accordance with an alternative embodiment of the invention. The system 150 includes a lead 152 that may be identical to that shown in FIGS. 6 and 7 except that instead of a bifurcated connector assembly at the proximal end of the lead, a single, compact coaxial or inline connector assembly 154, along the lines of the new IS-4 connector standard, connectable to an integrated pacemaker, therapeutic agent reservoir and EAP actuator drive unit 156, may be utilized.

The electroactive polymer cuffs used in the various embodiments of the invention may be preferably fabricated of any of the ionic EAP materials described in the "Background of the Invention", above. As explained, each cuff is preferably formed by coating it on the outer surface of the flexible, tubular body. Alternatively, each cuff may be fabricated as a separate, ring-like element slid to a predetermined position along the length of the tubular body. As a further alternative, FIG. 9 shows a flexible, tubular body 160 having mounted thereon an electroactive polymer actuator 162 representative of a series of actuators mounted on the body 160 to provide a peristaltic pumping action. The actuator 162 is in the form of a split ring or cuff having a generally longitudinally extending slit 164. The split ring EAP actuator 162 is easily slidable into position along the length of the tubular body 160. Electrical activation of the actuator 162 causes it to contract along the slit.

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

What is claimed is:

1. A peristaltic pump for conveying a fluid, the pump comprising:
    a flexible tube having an outer surface and a lumen for carrying the fluid, said tube having a length and opposed ends, the outer surface of the body carrying a plurality of longitudinally spaced-apart electroactive polymer actuators adapted to be responsive to electrical signals for energizing said plurality of electroactive polymer actuators sequentially to move a lumen pinch-off along the length of the tube to thereby convey the fluid from one end of the tube to the other end;
    wherein each of the plurality of electroactive polymer actuators encircles the outer surface of said tube; and wherein:
    each of the plurality of actuators comprises a split ring element mounted on the outer surface of the tube.

2. The pump of claim 1 wherein:
    the tube comprises a multi-lumen tubular body, one of the lumens of the multi-lumen body carrying said fluid, at least one of the remaining lumens containing electrical conductors connected to corresponding ones of the plurality of electroactive polymer actuators, said conductors being adapted to carry said electrical signals.

3. The pump of claim 1 wherein:
    each of the plurality of electroactive polymer actuators comprises an ionic electroactive polymer.

4. A system for conveying a fluid, the system comprising:
    a peristaltic pump comprising a flexible tube having an outer surface and a lumen for carrying the fluid, said tube having a length and opposed ends, the outer surface of the body carrying a plurality of longitudinally spaced-apart electroactive polymer actuators;
    an electrical power supply;
    a plurality of switches coupling the electrical power supply with the plurality of electroactive polymer actuators; and
    a controller connected to said plurality of switches for activating said switches to energize said plurality of electroactive polymer actuators sequentially to move a lumen pinch-off along the length of the tube to thereby convey the fluid from one end of the tube to the other end;
    each of the plurality of electroactive polymer actuators encircles the outer surface of said tube; and wherein:
    each of the plurality of actuators comprises a split ring element mounted on the outer surface of the tube.

5. The system of claim 4 wherein:
    the controller is programmable to control the energization parameters of said actuators.

6. The system of claim 4 wherein:
    each of the plurality of electroactive polymer actuators comprises an ionic electroactive polymer.

\* \* \* \* \*